(12) United States Patent
Cho

(10) Patent No.: US 8,852,529 B2
(45) Date of Patent: Oct. 7, 2014

(54) PARTICLE PROCESSING DEVICE USING CENTRIFUGAL FORCE

(75) Inventor: Young-Ho Cho, Daejeon (KR)

(73) Assignee: Nexvivo Co., Ltd., Daejeon (KR)

( * ) Notice: Subject to any disclaimer, the term of this patent is extended or adjusted under 35 U.S.C. 154(b) by 53 days.

(21) Appl. No.: 13/583,104

(22) PCT Filed: Aug. 5, 2010

(86) PCT No.: PCT/KR2010/005127
§ 371 (c)(1),
(2), (4) Date: Sep. 6, 2012

(87) PCT Pub. No.: WO2011/111909
PCT Pub. Date: Sep. 15, 2011

(65) Prior Publication Data
US 2012/0325347 A1    Dec. 27, 2012

(30) Foreign Application Priority Data
Mar. 10, 2010    (KR) ........................ 10-2010-0021258

(51) Int. Cl.
G01N 15/04        (2006.01)
B01L 3/00         (2006.01)
G01N 21/07        (2006.01)
B81B 3/00         (2006.01)

(52) U.S. Cl.
CPC ......... *G01N 21/07* (2013.01); *B01L 2300/0803* (2013.01); *B01L 2200/0668* (2013.01); *B01L 2400/0409* (2013.01); *B01L 3/502753* (2013.01); *B81B 3/004* (2013.01); *B01L 2400/082* (2013.01); *B01L 2400/086* (2013.01); *B01L 3/502746* (2013.01); *B01L 2300/123* (2013.01); *B01L 2300/0864* (2013.01); *B01L 2200/0652* (2013.01); *B01L 3/502761* (2013.01)
USPC ........ 422/506; 422/548; 422/551; 435/286.5; 435/287.3; 435/288.4; 210/189; 210/520; 210/800; 210/801

(58) Field of Classification Search
None
See application file for complete search history.

(56) References Cited

U.S. PATENT DOCUMENTS

| 5,693,233 | A  |    | 12/1997 | Schembri |
|-----------|----|----|---------|----------|
| 5,910,288 | A  | *  | 6/1999  | Schembri .................... 422/551 |
| 7,857,141 | B2 |    | 12/2010 | Park et al. |
| 2008/0035579 | A1 |    | 2/2008 | Lee et al. |
| 2008/0135462 | A1 |    | 6/2008 | Park et al. |
| 2008/0226504 | A1 |    | 9/2008 | Park |
| 2008/0237151 | A1 |    | 10/2008 | Cho |

FOREIGN PATENT DOCUMENTS

JP        2008-145420        6/2008

* cited by examiner

*Primary Examiner* — Jill Warden
*Assistant Examiner* — Timothy G Kingan
(74) *Attorney, Agent, or Firm* — Fildes & Outland, P.C.

(57) ABSTRACT

A particle processing device includes a substrate and at least one fluidic path. The substrate is rotatable with respect to the middle region thereof. The fluidic path is provided in the substrate to extend from the middle region to a peripheral region. The fluidic path transfers a fluid having a particle from an input portion to an output portion of the fluidic pather by using a centrifugal force of the rotation of the substrate. A capturing region is formed between the input portion and the output portion of the fluidic path to have a changeable sectional shape for capturing the particle.

16 Claims, 12 Drawing Sheets

PARTICLE PROCESSING DEVICE USING CENTRIFUGAL FORCE

CLAIM OF PRIORITY

This application claims priority under 35 USC §119 to Korean Patent Application No. 2010-0021258, filed on Mar. 30, 2011 in the Korean Intellectual Property Office (KIPO), the contents of which are herein incorporated by reference in their entirety.

BACKGROUND

1. Field

Example embodiments relate to a particle processing device. More particularly, example embodiments relate to a particle processing device using centrifugal force.

2. Description of the Related Art

Generally, in order to process a fluid having particles, a particle processing device may include various pressure sources such as a syringe pump, a peristaltic pump, a gas pump, etc. However, an expensive external precise pump or a complex integrated micro-pump may be required for these types of the pressure sources.

Recently, technologies for transferring a fluid by using a centrifugal force of the rotation of a substrate including a fluidic path formed therein have been developed. The particle processing device using the technologies may be manufactured by simple processes without the expensive micro-pump, to thereby reduce the manufacturing cost. However, since the conventional particle processing device is dedicated only for the fluid transfer, an actuator or valve using a pneumatice pressure or surface tension may be required for the device to control the fluid flow in order to process particles in the fluid.

SUMMARY

Example embodiments provide a particle processing device capable of selectively separating and collecting particles in a fluid by using a centrifugal force.

According to example embodiments, there is provided a particle processing device. The device includes a substrate and at least one fluidic path. The substrate is rotatable with respect to the middle region thereof. The fluidic path is provided in the substrate to extend from the middle region to a peripheral region. The fluidic path transfers a fluid having a particle from an input portion to an output portion of the fluidic pather by using a centrifugal force of the rotation of the substrate. A capturing region is formed between the input portion and the output portion of the fluidic path to have a changeable sectional shape for capturing the particle.

In example embodiments, the sectional area of the capturing region may be decreased gradually along the extending direction of the fluidic path. The capturing region may have a sectional dimension smaller than the minimum size of the particle that is deformed under a local pressure due to the physical characteristics of the particle such as deformability or stiffness.

In example embodiments, the sectional shape of the fluidic path may be symmetric or asymmetric.

In example embodiments, the fluidic path may extend to be straight or spiral from the middle region to the peripheral region of the substrate.

In example embodiments, the rotational velocity, rotational acceleration or rotational direction of the substrate may be changed to control the flow velocity of the fluid.

In example embodiments, the fluidic path may be a flexible fluidic path. The sectional shape of the flexible fluidic path may be symmetric or asymmetric. The flexible fluidic path may extend to be straight or spiral from the middle region to the peripheral region of the substrate.

In example embodiments, the device may further include a flexible layer that forms a sidewall of the flexible fluidic path and defines the capturing region. The flexible layer may include a fixing portion fixed to a sidewall of the fluidic path and a moving portion extending from the fixing portion and configured to be bent by the rotation of the substrate.

In example embodiments, the rotational velocity, rotational acceleration or rotational direction of the substrate may be changed to control the sectional area of the fluidic path and the flow velocity of the fluid.

In example embodiments, a plurality of the fluidic paths may be provided in parallel with one another in the substrate. The device may further include a common input/output portion that is provided in the middle region of the substrate to be connected to the input portions of the fluidic paths.

In example embodiments, the device may further include a counter that is arranged in any one of the input portion and the output portion of the fluidic path to detect the number of the particles.

In example embodiments, a collecting fluid may flow from the output portion to the input portion of the fluidic path to collect the particle that is captured in the capturing region of the fluidic path.

In example embodiments, a biochemical material layer may be formed on an inner surface of the fluidic path or the inner surface of the fluidic path may be biochemically or physically changed in order to increase or decrease the adhesive strength with the particle.

According to example embodiments, the particle processing device may include a fluidic path in a rotatable substrate, through which a fluid having particles flows. The fluidic path may be a stationary or flexible fluidic path having a changeable sectional shape. Accordingly, the rotational velocity, rotational acceleration and rotational direction of the substrate may be controlled, to thereby efficiently transfer and separate the target particle from the fluid. Thus, the particle processing device may be manufactured by simple processes without performing complicate processes for manufacturing a micro-pump, to thereby reduce the manufacturing cost.

In addition, a plurality of the fluidic paths may be connected in parallel to the common input/output portion to increase the analysis speed for the micro-particle. Further, a counter may be provided in the input portion or the output portion of the fluidic path to conduct quantitative analysis and a collection fluid may be used to collect the captured particle in the common input/ouput portion.

BRIEF DESCRIPTION OF THE DRAWINGS

Example embodiments will be more clearly understood from the following detailed description taken in conjunction with the accompanying drawings. FIGS. 1 to 10 represent non-limiting, example embodiments as described herein.

FIG. 1 is a plan view illustrating a particle processing device in accordance with a first example embodiment.

FIG. 2 is a plan view illustrating a fluidic path of the particle processing device in FIG. 1.

FIG. 3 is a cross-sectional view taken along the line in FIG. 2.

FIG. 4 is a capturing region of the fluidic path in FIG. 1.

FIG. 5 is a plan view illustrating a particle processing device in accordance with a second example embodiment.

FIG. 7 is a plan view illustrating a particle processing device in accordance with a third example embodiment.

FIG. 8 is a cross-sectional view illustrating a fluidic path of the particle processing device in FIG. 7.

FIG. 10 is a plan view illustrating a particle processing device in accordance with a fourth example embodiment.

DESCRIPTION OF EMBODIMENTS

Figure 1:
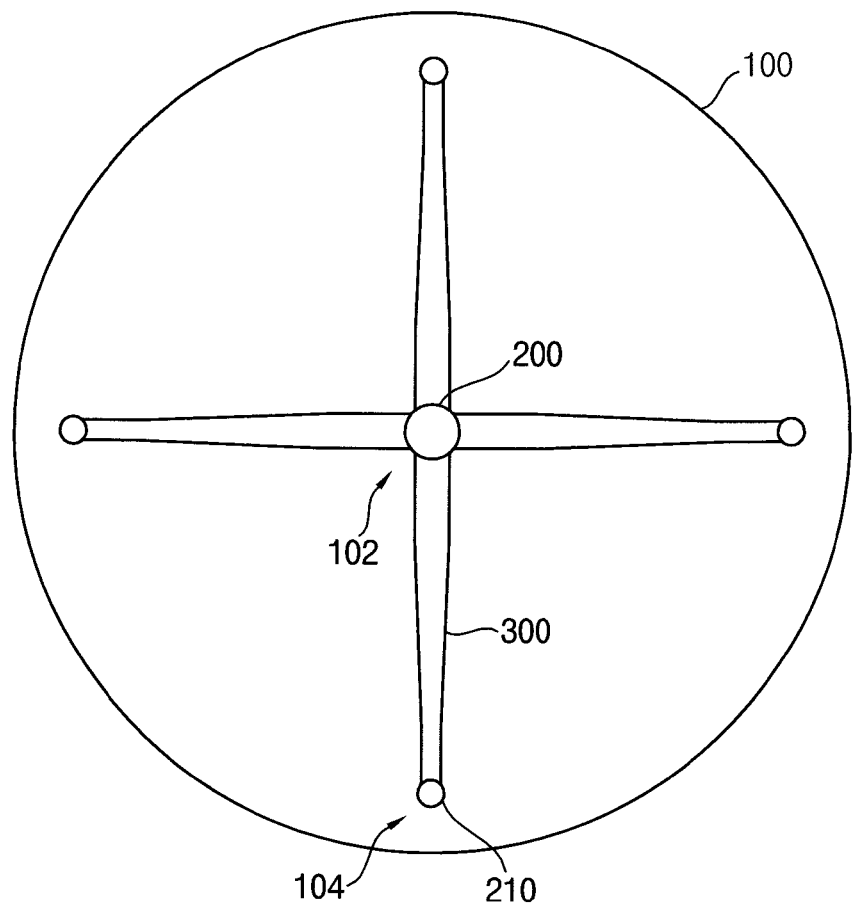

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this description will be thorough and complete, and will fully convey the scope of the present inventive concept to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, fourth etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concept.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
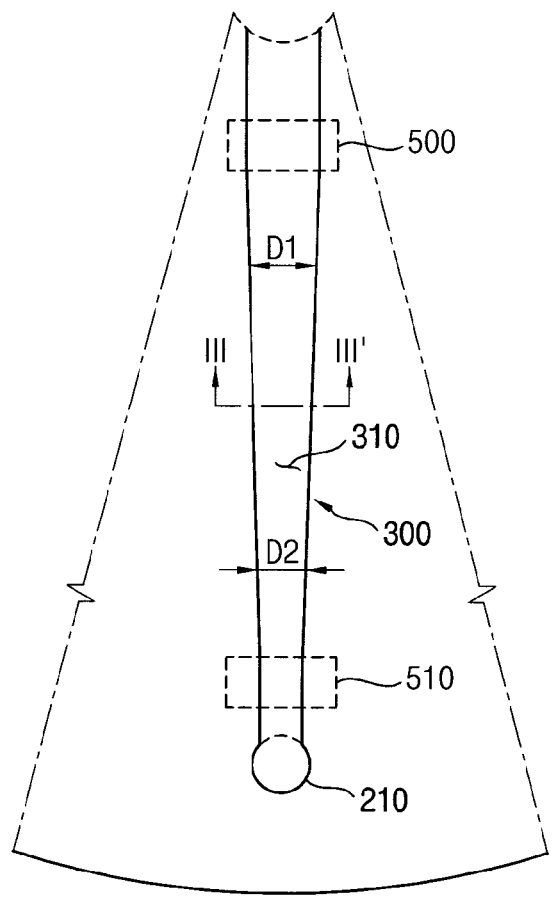
Figure 3:
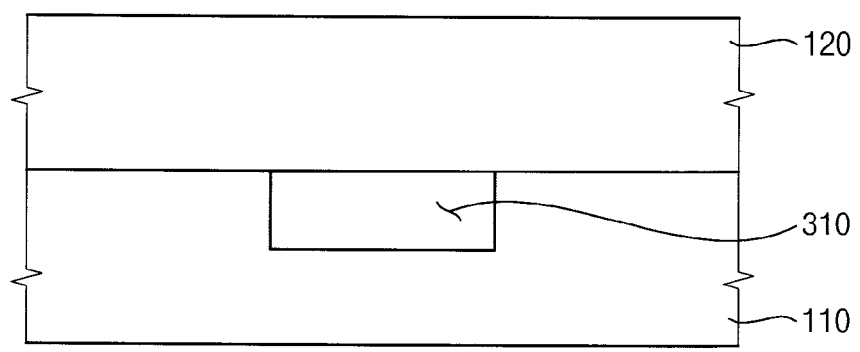
Figure 4:
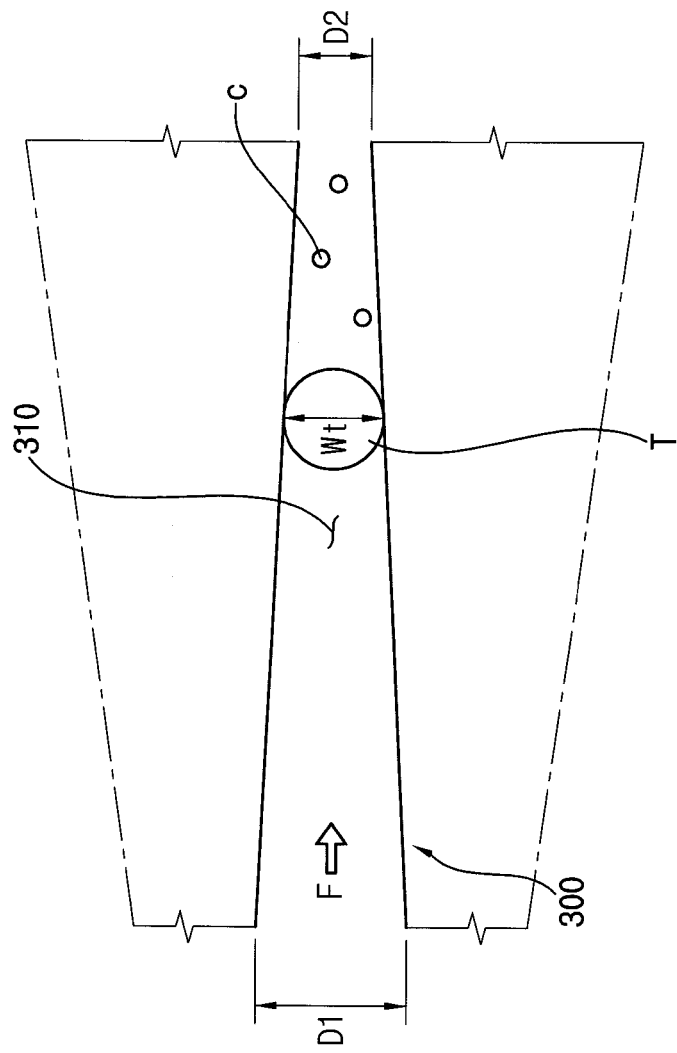

FIG. 1 is a plan view illustrating a particle processing device in accordance with a first example embodiment. FIG. 2 is a plan view illustrating a fluidic path of the particle processing device in FIG. 1. FIG. 3 is a cross-sectional view taken along the line in FIG. 2. FIG. 4 is a capturing region of the fluidic path in FIG. 1.

Referring to FIGS. 1 to 4, a particle processing device 10 may include a rotatable substrate 100 and at least one fluidic path provided in the substrate 100.

The substrate 100 may include a channel array in a radial direction. The channel array may have at least one fluidic path 300 extending from the middle region 102 to a peripheral region 104. For example, the substrate 100 may be a disk-shaped rotational body having the center axis at the middle region 102. Accordingly, the substrate 100 may be rotatable with respect to the center axis at the middle region 102.

In a first example embodiment, at least one fluidic path 300 may be provided in the substrate 100. The fluidic path 300 may be formed to extend in a radial direction from the middle region 102. The fluidic path 300 may be straight from the middle region 102 to the peripheral region 104.

A first port 200 may be provided in the middle region of the substrate 100. A fluid may flow into or out of the device 10 through the first port 200. A second port 210 may be provided in the peripheral region 104 of the substrate 100. A fluid may flow into or out of the device 10 through the second port 210. An end portion, an input portion of the fluidic path 300 may be connected to the first port 200. Another end portion, an output portion of the fluidic path 300 may be connected to the second port 210.

In this embodiment, four fluidic paths 300 may be connected in parallel to the first port 200. In this case, the first port 200 may serve as a common input/output portion for the four fluidic paths 300. The four fluidic paths 300 may extend in the radial direction from the first port 200 to be connected to four second ports 210, respectively. However, it can be understood that the number and the shape of the paths 300 may not be limited thereto.

In a first example embodiment, the particle processing device 10 may include a fluid supply element for supplying a fluid to the first port 200. The fluid supply element may be connected to the first port 200 to supply a fluid having particles to the fluidic path 300.

The particle processing device 10 may include a fluid collection element for collecting the particles that are selectively captured in the fluidic path 300. The fluid collection element may be connected to the ports to collect the selectively captured particles.

For example, the fluid may be a body fluid such as blood including cells of different types and biological particles. The fluid may include a target particle having information about the health of an organism. The target particle may be a biological micro-particle such as cell, bacteria, virus, etc.

In a first example embodiment, the particle processing device 10 may include a driving portion (not illustrated) that is connected to the substrate 100. The driving portion may include a drive shaft (not illustrated) for rotating the substrate 100 with respect to the center axis and a driving motor (not illustrated) for driving the drive shaft. Alternatively, the drive shaft may be connected to the peripheral region 104 of the substrate 100 so that the rotational axis of the substrate 100 may be positioned in the peripheral region 104, not the middle region 102. Accordingly, the driving portion may be connected to the middle region 102 or to a peripheral region of the substrate 100, to control the rotational position and velocity of the substrate 100.

As illustrated in FIG. 2, a capturing region 310 having a changeable sectional shape may be formed between the input portion and the output portion of the fluidic path 300 to capture the target particles in a fluid. For example, the sectional area of the capturing region 310 may be decreased gradually in a flow direction of a fluid, that is, along the extending direction of the fluidic path.

The capturing region 310 of the fluidic path 300 may have a first sectional area at a position relatively adjacent to the first port 200. The capturing region 310 of the first sectional area may have a first diameter (D1) or a first width. The capturing region 310 of the fluidic path 300 may have a second sectional area at a position relatively adjacent to the second port 210. The second sectional area is smaller than the first sectional area. The capturing region 310 of the second sectional area may have a second diameter (D2) smaller than the first diameter (D1) or a second width smaller than the first width. Accordingly, the sectional profile of the capturing region 310 may be decreased gradually in a flow direction of a fluid. That is, the capturing region 310 may have a changeable sectional shape, the sectional area of which is decreased gradually in the flow direction for capturing particles.

In a first example embodiment, the minimum dimension of the capturing region 310 may be smaller than the minimum size of the particle that is deformed due to the physical characteristics of the particle such as deformability or stiffness. For example, the dimension of the capturing region 310 having the second diameter (D2) may be smaller than the minimum size of the target particle that is deformed under a local pressure due to the physical characteristics of the particle such as deformability or stiffness.

As illustrated in FIG. 3, the substrate 110 may include a first substrate 110 and a second substrate 120. The second substrate 120 is formed on the first substrate 110 to form the fluidic path 300 between the first and second substrates 110, 120. A trench may be formed in the first substrate 110 to extend from the first port 200 to the second port 210. The changeable sectional shape of the capturing region 310 may be defined by first and second sidewalls of the trench opposite to each other. The first and second sidewalls of the treanch may be formed symmetrically to form the capturing region 310 of the fluidic path 300.

The fluidic paths may be formed by semiconductor manufacture processes including photolithography, growth and etching of crystal structure. For example, the first and second substrates may be formed using polymer material, inorganic material, etc. Examples of the polymer material may be PDMS (polydimethylsiloxane), PMMA (polymethylmethacrlyate), etc. The examples of the inorganic material may be glass, quartz, silicon, etc.

For example, the capturing region 310 of the fluidic path 300 may have a rectangle sectional shape. However, it can be understood that the capturing region 310 may have various sectional shapes such as circle, ellipse, etc according to the shape of the trench.

As illustrated in FIG. 4, after a fluid having particles is supplied to the first portion 200 of the substrate 100, the substrate 100 may rotate about the center axis at the middle region 102. Thus, the fluid may move from the input portion to the output portion of the fluidic path 300 by the centrifugal force of the rotation of the substrate 100.

In a first example embodiment, the target particle in the fluid may have a diameter (Wt) greater than other particles (C). Accordingly, the other particles (C) except the target particle may flow out of the capturing region 310 of the fluidic path 300 and then move to the second port 210.

The target particle may have deformability under the local pressure in the fluidic path 300 due to the centrifugal force. After the target particle having deformability enters the capturing region 310 of the fluidic path 300, the target particle may be captured between a first opening having the first diameter (D1) and a second opening having the second diameter (D2) in the capturing region 310. The second diameter (D2) may be smaller than the minimum diameter of the target particle that is deformed by the local pressure. The first diameter (D1) may be greater than the minimum diameter of the deformed target particle. In here, the capturing position of the target particle in the capturing region 310 may be determined according to the physical characteristics such as deformability or stiffness.

Then, in order to collect the captured particle, a collecting fluid may flow from the second port 210 to the first port 200 through the fluidic path 300. Accordingly, the captured particle may be collected in the fluid collection element.

In a first example embodiment, the particle processing device 10 may further include a counter for detecting the number of the particles that are selectively captured. For example, a first counter 500 may be provided in the input portion of the fluidic path 300 adjacent to the first port 200. A second counter 510 may be provided in the output portion of the fluidic path 300 adjacent to the second port 210. Alternatively, one counter may be arranged in any one of the input portion and the output portion of the fluidic path 300.

In a first example embodiment, a biochemical material layer may be formed on an inner surface of the fluidic path 300 in order to increase or decrease the adhesive strength with the target particle. Alternatively, the inner surface of the fluidic path 300 may be biochemically or physically changed in order to increase or decrease the adhesive strength with the target particle. The biochemical material layer may include a material that induces an antigen-antibody reaction.

As mentioned above, the driving portion of the particle processing device 10 may change the rotational velocity, rotational acceleration and rotational direction of the substrate 100 to thereby control the flow velocity of the fluid. Accordingly, the fluid may move from the input portion to the output portion of the fluidic path 300 by the centrifugal force of the rotation of the substrate 100 so that the particle processing device 10 may selectively capture the target particle in the fluid according to the size and deformability thereof.

Figure 5:
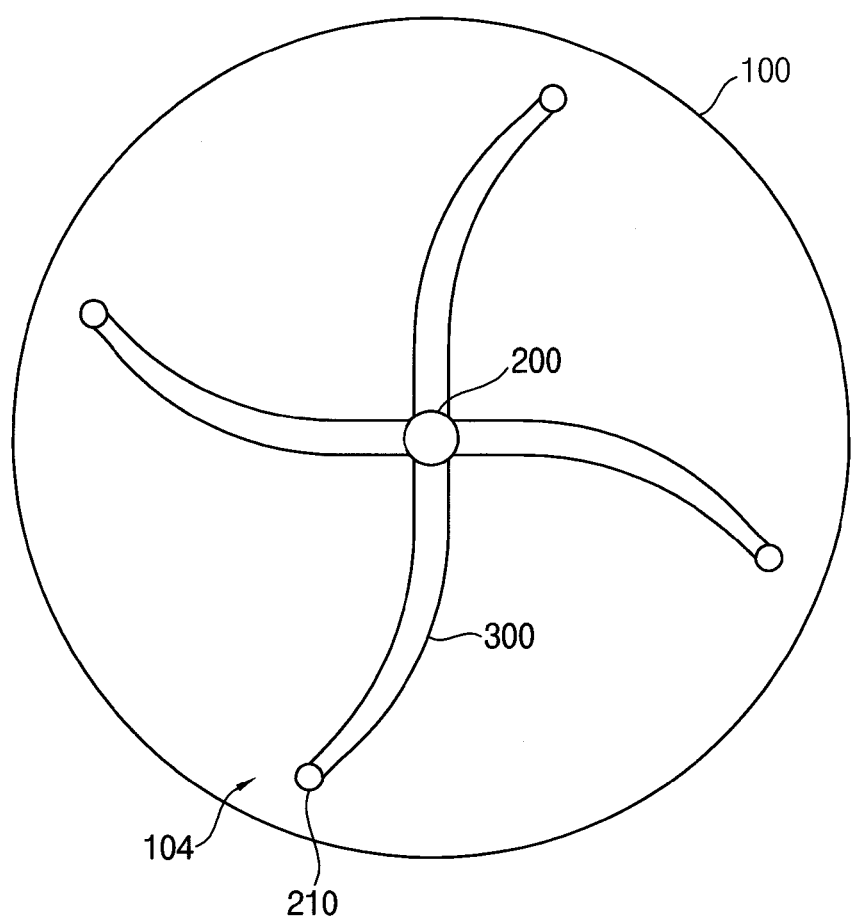

FIG. 5 is a plan view illustrating a particle processing device in accordance with a second example embodiment. The present embodiment may be substantially the same as in the first example embodiment of FIG. 1 except for the extending direction of the fluidic path. Thus, the same reference numerals will be used to refer to the same or like elements as those described in the first example embodiment and any further repetitive explanation concerning the above elements will be omitted.

Referring to FIG. 5, a particle processing device 11 according to a second example embodiment may include at least one curvilinear fluidic path 300 in a substrate 100.

In a second example embodiment, the fluidic path 300 may have a spiral shape extending from the middle region 102 to a peripheral region 104. The fluidic path 300 may extend from the middle region 102 to the peripheral region 104 of the substrate 100 in a radial direction as well as a circumferential direction.

Figure 6A:
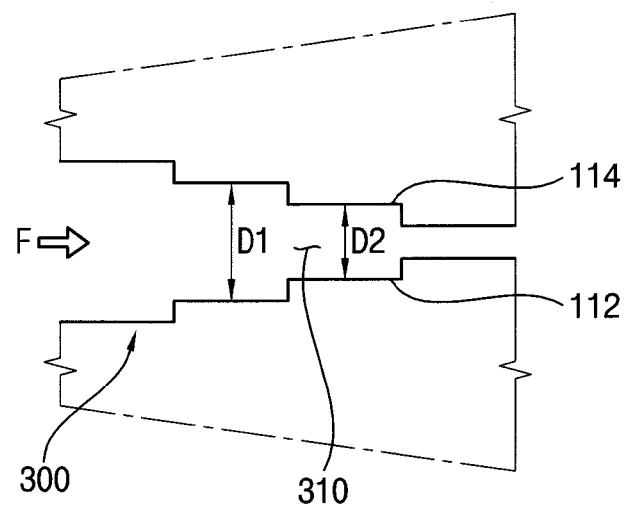
FIGS. 6A to 6E are cross-sectional views illustrating various shapes of a fluidic path.
Figure 6B:
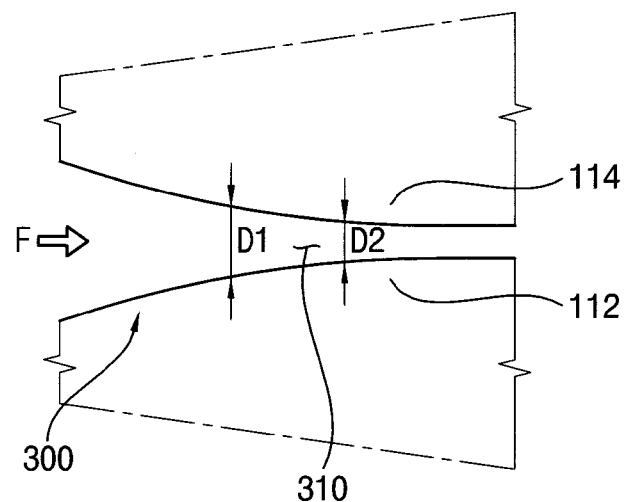
Figure 6C:
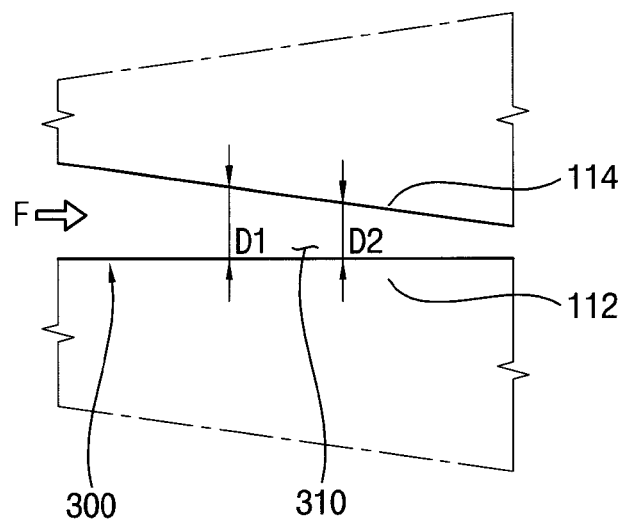
Figure 6D:
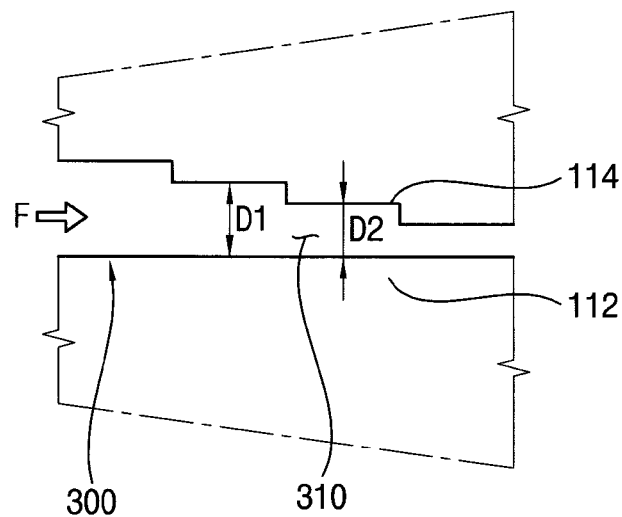
Figure 6E:
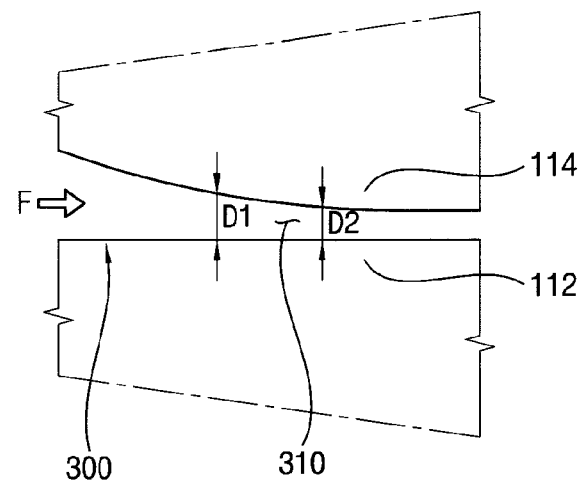

FIGS. 6A to 6E are cross-sectional views illustrating various shapes of a fluidic path. FIGS. 6A and 6B are cross-sectional views illustrating a symmetric fluidic path. FIGS. 6C to 6E are cross-sectional views illustrating an asymmetric fluidic path.

Referring to FIG. 6A, a trench may be formed in substrate 100 to define a capturing region 310 of the fluidic path 300. The trench may have opposing first and second sidewalls 112, 114 that define the capturing region 310. The first and second sidewalls 112, 114 may be symmetric to each other. The first and second sidewalls 112, 114 may be formed to have stepped portions such that the capturing region 310 may have a step-wisely decreasing sectional shape.

Referring to FIG. 6B, the first and second sidewalls 112, 114 may be symmetric to each other. The first and second sidewalls 112, 114 may be formed to be curvilinear such that the capturing region 310 may have a continuously decreasing sectional shape.

Referring to FIG. 6C, the first and second sidewalls 112, 114 may be asymmetric to each other. The first and second sidewalls 112, 114 may be formed to be linear such that the capturing region 310 may have a continuously decreasing sectional shape.

Referring to FIG. 6D, the first and second sidewalls 112, 114 may be asymmetric to each other. The first sidewall 112 may be formed to be linear and the second sidewall 114 may be formed to have stepped portions such that the capturing region 310 may have a stepwisely decreasing sectional shape.

Referring to FIG. 6E, the first and second sidewalls 112, 114 may be asymmetric to each other. The first sidewall 112 may be formed to be linear and the second sidewall 114 may be formed to be curvilinear such that the capturing region 310 may have a continuously decreasing sectional shape.

Figure 7:
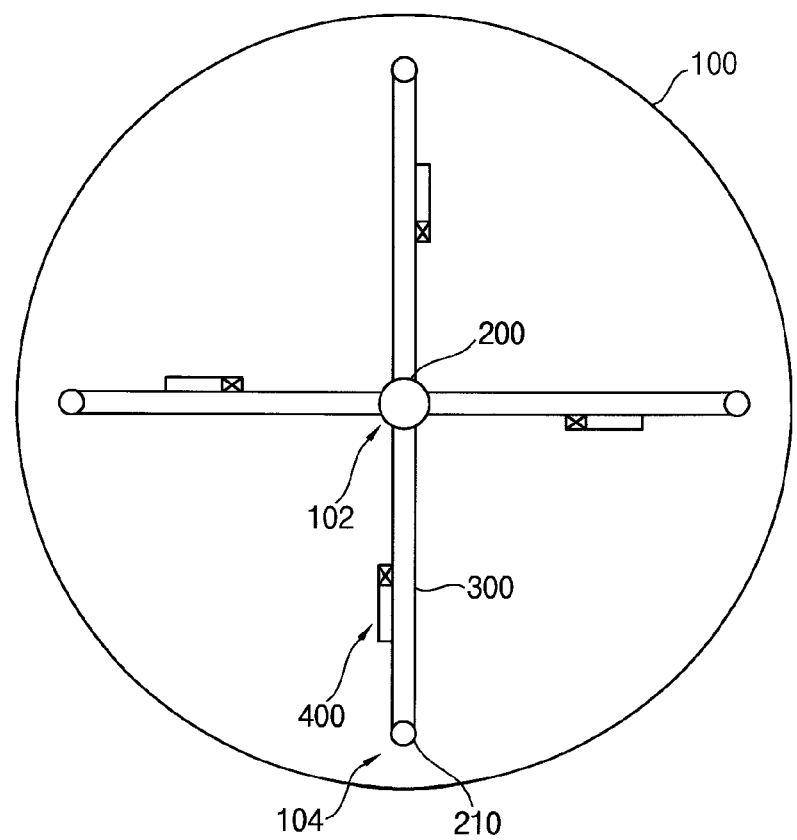
Figure 8:
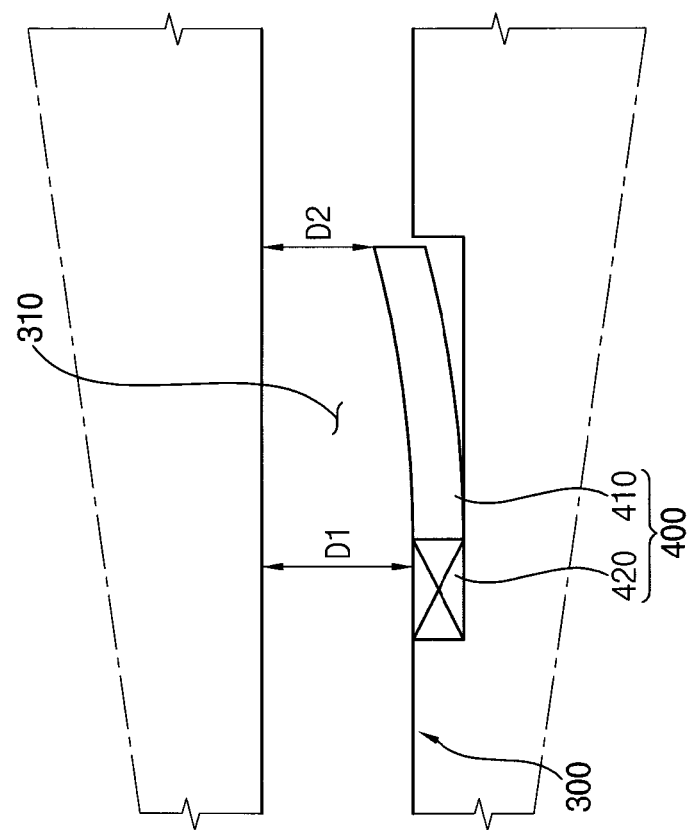

FIG. 7 is a plan view illustrating a particle processing device in accordance with a third example embodiment. FIG. 8 is a cross-sectional view illustrating a fluidic path of the particle processing device in FIG. 7. The present embodiment may be substantially the same as in the first example embodiment of FIG. 1 except for the structure of the fluidic path. Thus, the same reference numerals will be used to refer to the same or like elements as those described in the first example embodiment and any further repetitive explanation concerning the above elements will be omitted.

Referring to FIGS. 7 and 8, a particle processing device 12 according to a third example embodiment may include at least one flexible fluidic path in a substrate 100.

In a third example embodiment, a fluidic path 300 may extend in a radial direction form the middle region 102 to a peripheral region 104. The fluidic path 300 may have a uniform sectional shape having a constant width and height along the extending direction thereof. The fluidic path 300 may be straight from the middle region 102 to the peripheral region 104.

The particle processing device 12 may include a flexible layer 400 that forms a sidewall of the flexible fluidic path and defines a capturing region 310. The flexible layer 400 may include a moving portion 410 and a fixing portion 420. The fixing portion 420 may be fixed to a sidewall of the fluidic path 300. The moving portion 410 may extend from the fixing portion 420. The moving portion 410 may be bent by the rotation of the substrate 100 to define the capturing region 310. The fixing portion 420 may be provided at a position relatively adjacent to the first port 200 and the moving portion 410 may be provided at a position relatively adjacent to the second port 210.

In a third example embodiment, the moving portion 410 may be deformed by the rotation of the substrate 100. Alternatively, the flexible layer may constitute a sidewall membrane of a pneumatic membrane path that is formed in the sidewall of the fluidic path 300. In this case, the flexible layer serving as a membrane may be deformed to expand laterally by a predetermined pneumatic pressure that is supplied into the pneumatic membrane path, to form the capturing region 310.

Accordingly, by controlling the rotational velocity, rotational acceleration and rotational direction of the substrate 100, the moving portion 410 may be bent inward in the fluidic path 300 to change the sectional area (width or height) of the fluidic path 300. Thus, the capturing region 310 of the flexible fluidic path may be formed by the deformation of the flexible layer 400 due to the centrifugal force.

Figure 9A:
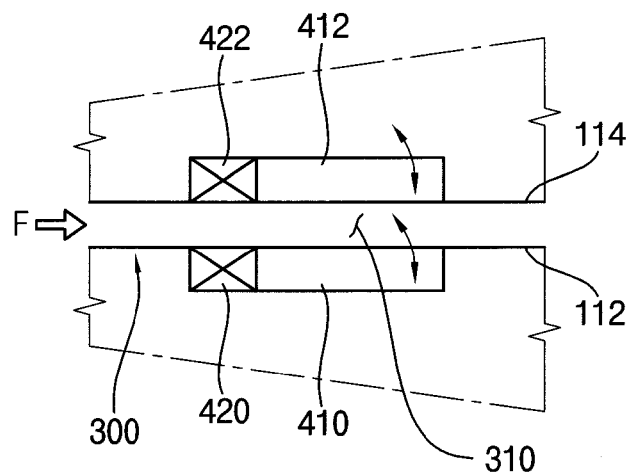
FIGS. 9A to 9G are cross-sectional views illustrating various shapes of a flexible fluidic path.
Figure 9B:
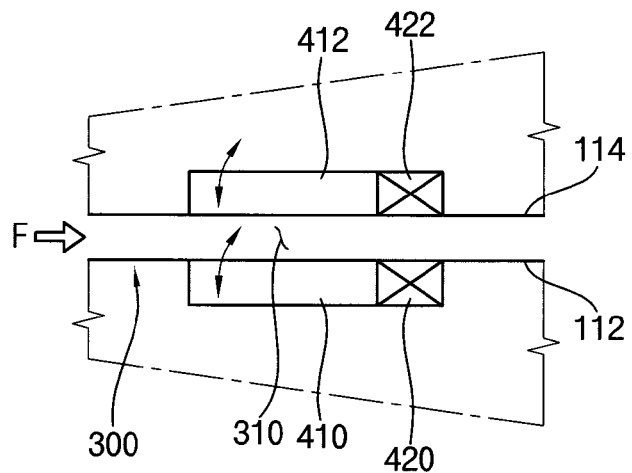
Figure 9C:
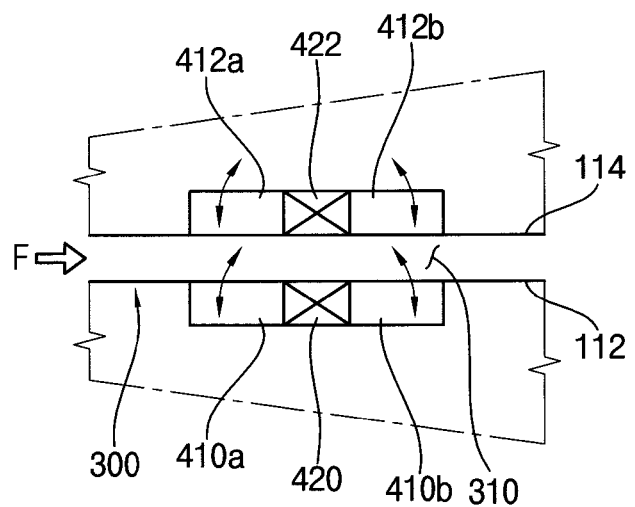

FIGS. 9A to 9G are cross-sectional views illustrating various shapes of a flexible fluidic path. FIGS. 9A to 9C are cross-sectional views illustrating a symmetric flexible fluidic path. FIGS. 9D to 9G are cross-sectional views illustrating an asymmetric flexible fluidic path.

Referring to FIG. 9A, first and second flexible layers may be provided in opposing first and second sidewalls 112, 114 of a trench formed in a substrate 100. The first and second flexible layers may be symmetric to each other.

A first fixing portion 420 of the first flexible layer may be fixed to the first sidewall 112 and a first moving portion 410 of the first flexible layer may extend from the first fixing portion 420 to form a sidewall of a flexible fluid path. The first fixing portion 420 may be provided at a position relatively adjacent to a first port 200 and the first moving portion 410 may be provided at a position relatively adjacent to a second port 210.

A second fixing portion 422 of the second flexible layer may be fixed to the second sidewall 114 and a second moving portion 412 of the second flexible layer may extend from the second fixing portion 422 to form another sidewall of the flexible fluid path. The second fixing portion 422 may be provided at a position relatively adjacent to the first port 200 and the second moving portion 412 may be provided at a position relatively adjacent to the second port 210.

The first moving portion 410 may have the same deformability as the second moving portion 412. Alternatively, the first moving portion 410 may have different deformability from the second moving portion 412.

Accordingly, the first and second flexible layers formed in the first and second sidewalls 112, 114 of the fluidic path 300 may be deformed by the rotation of the substrate 100 such that the capturing region 310 may have a changeable sectional shape.

Referring to FIG. 9B, first and second flexible layers may be provided in opposing first and second sidewalls 112, 114 of a trench formed in a substrate 100. The first and second flexible layers may be symmetric to each other.

A first moving portion 410 of the first flexible layer may be provided at a position relatively adjacent to the first port 200 and a first fixing portion 420 of the first flexible layer may be provided at a position relatively adjacent to the second port 210. A second moving portion 412 of the second flexible layer may be provided at a position relatively adjacent to the first port 200 and a second fixing portion 422 of the second flexible layer may be provided at a position relatively adjacent to the second port 210.

Referring to FIG. 9C, first and second flexible layers may be provided in opposing first and second sidewalls 112, 114 of a trench formed in a substrate 100. The first and second flexible layers may be symmetric to each other.

A first fixing portion 420 of the first flexible layer may be fixed to the first sidewall 112. First moving portions 410a, 410b of the first flexible layer may be provided in both sides of the first fixing portion 420 to form a sidewall of a flexible fluid path.

A second fixing portion 422 of the second flexible layer may be fixed to the second sidewall 114. Second moving portions 412a, 412b of the second flexible layer may be provided in both sides of the second fixing portion 422 to form another sidewall of the flexible fluid path.

Accordingly, the first and second flexible layers formed in the first and second sidewalls 112, 114 of the fluidic path 300 may be deformed by the rotation of the substrate 100 such that the capturing region 310 may have a changeable sectional shape.

Figure 9D:
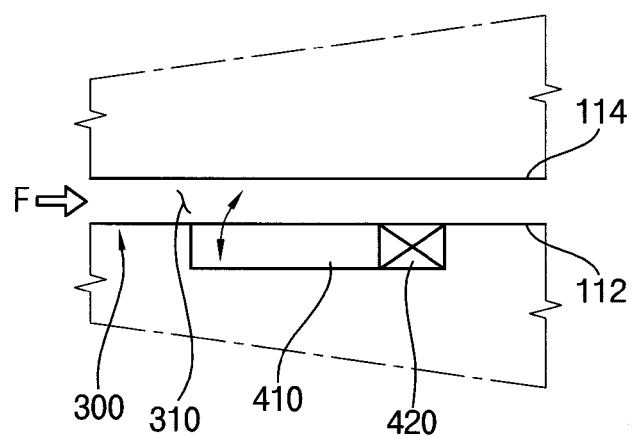

Referring to FIG. 9D, an asymmetric flexible layer may be provided in a first sidewall 112 of a trench in a substrate 100. A fixing portion 420 of the flexible layer may be fixed to the first sidewall 112. A moving portion 410 of the flexible layer may extend from the fixing portion 420 to form a sidewall of a flexible fluidic path. The fixing portion 420 may be provided at a position relatively adjacent to the first port 200.

Figure 9E:
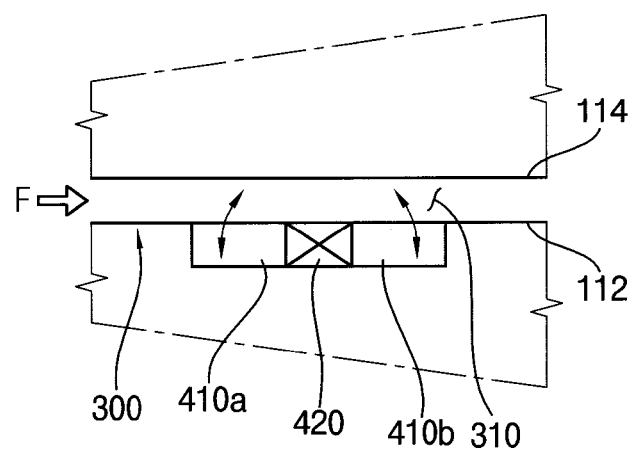

Referring to FIG. 9E, an asymmetric flexible layer may be provided in a first sidewall 112 of a trench in a substrate 100. A fixing portion 420 of the flexible layer may be fixed to the first sidewall 112. Moving portions 410a, 410b of the first flexible layer may be provided in both sides of the fixing portion 420 to form a sidewall of a flexible fluid path.

Figure 9F:
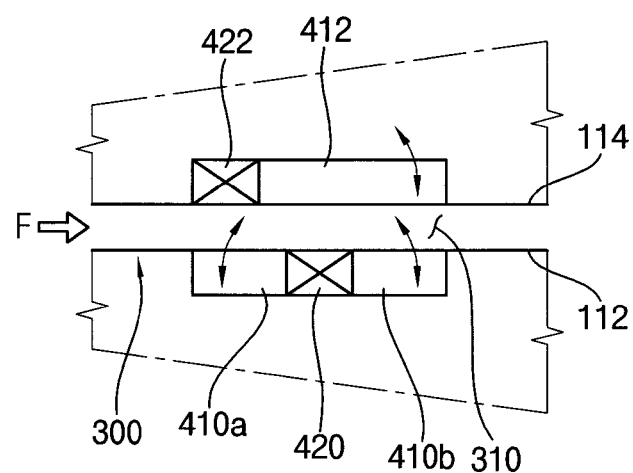

Referring to FIG. 9F, first and second flexible layers may be provided in opposing first and second sidewalls 112, 114 of a trench formed in a substrate 100. The first and second flexible layers may be asymmetric to each other.

A first fixing portion 420 of the first flexible layer may be fixed to the first sidewall 112. First moving portions 410a, 410b of the first flexible layer may be provided in both sides of the first fixing portion 420 to form a sidewall of a flexible fluidic path.

A second fixing portion 422 of the second flexible layer may be fixed to the second sidewall 114. A second moving portion 412 of the second flexible layer may extend from the second fixing portion 422 to form another sidewall of the flexible fluidic path. The second fixing portion 422 may be provided at a position relatively adjacent to the first port 200.

Figure 9G:
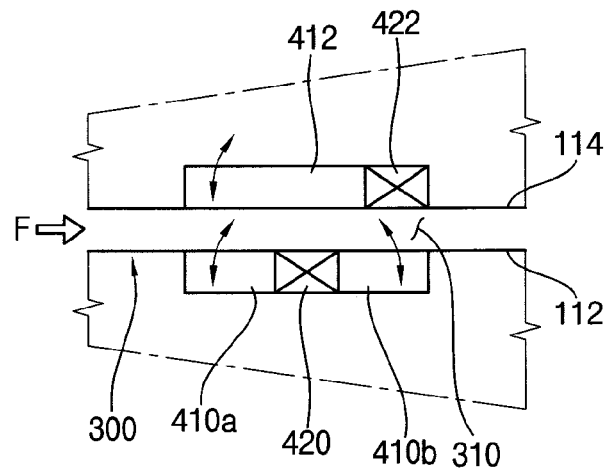

Referring to FIG. 9G first and second flexible layers may be provided in opposing first and second sidewalls 112, 114 of a trench formed in a substrate 100. The first and second flexible layers may be asymmetric to each other.

A first fixing portion 420 of the first flexible layer may be fixed to the first sidewall 112. First moving portions 410a, 410b of the first flexible layer may be provided in both sides of the first fixing portion 420 to form a sidewall of a flexible fluidic path.

A second fixing portion 422 of the second flexible layer may be fixed to the second sidewall 114. A second moving portion 412 of the second flexible layer may extend from the second fixing portion 422 to form another sidewall of the flexible fluidic path. The second moving portion 412 may be provided at a position relatively adjacent to the first port 200.

Figure 10:
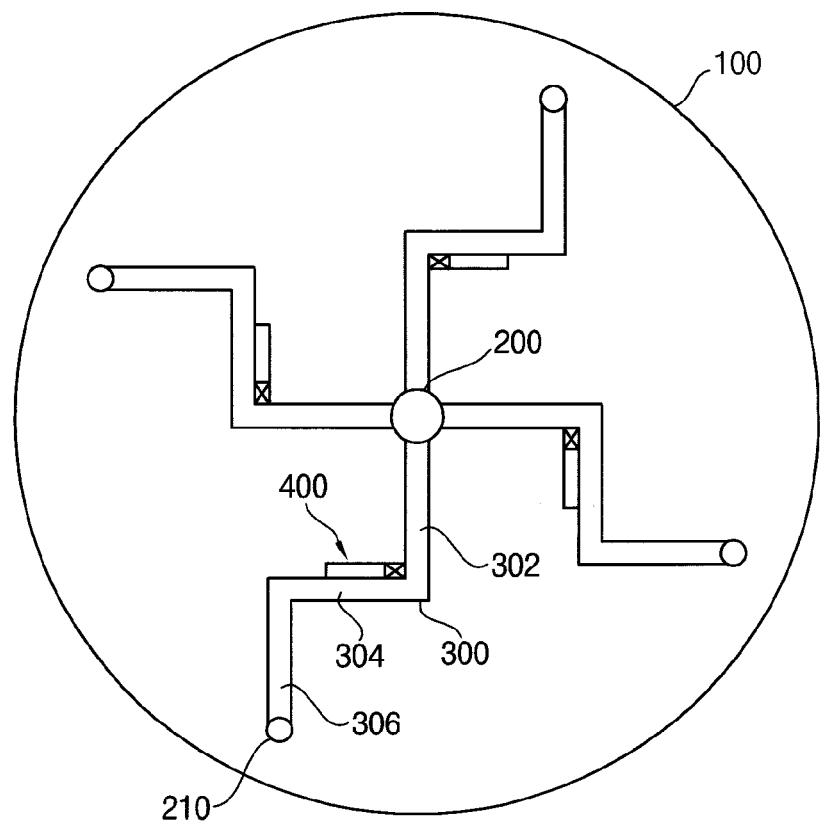

FIG. 10 is a plan view illustrating a particle processing device in accordance with a fourth example embodiment. The present embodiment may be substantially the same as in the third example embodiment of FIG. 7 except for the extending direction of the fluidic path. Thus, the same reference numerals will be used to refer to the same or like elements as those described in the third example embodiment and any further repetitive explanation concerning the above elements will be omitted.

Referring to FIG. 10, a particle processing device 13 according to a fourth example embodiment may include at least one flexible fluidic path in a substrate 100.

In a fourth example embodiment, a fluidic path 300 may extend from the middle region 102 of the substrate 100 in a radial direction as well as a circumferential direction. The fluidic path 300 may include first, second and third paths 302, 304, 306.

The first path 302 may extend from a first port 200 in the radial direction. The second path 304 may extend from an end portion of the first path 302 in the circumferential direction. The third path 306 may extend from an end portion of the second path 304 in a direction perpendicular to the extending direction of the second path 304 to be connected to a second port 210. Accordingly, the fluidic path 300 may extend like a spiral shape.

As illustrated in FIG. 10, a flexible layer 400 may be provided in a sidewall of the second path 304 to provide a capturing region having a changeable sectional shape.

According to example embodiments, the particle processing device may include a fluidic path in a rotatable substrate, through which a fluid having particles flows. The fluidic path may be a stationary or flexible fluidic path having a changeable sectional shape. Accordingly, the rotational velocity, rotational acceleration and rotational direction of the substrate may be controlled, to thereby efficiently transfer and separate the target particle from the fluid. Thus, the particle processing device may be manufactured by simple processes without performing complicate processes for manufacturing a micro-pump, to thereby reduce the manufacturing cost.

In addition, a plurality of the fluidic paths may be connected in parallel to the common input/output portion to increase the analysis speed for the micro-particle. Further, a counter may be provided in the input portion or the output portion of the fluidic path to conduct quantitative analysis and a collection fluid may be used to collect the captured particle in the common input/ouput portion.

The foregoing is illustrative of example embodiments and is not to be construed as limiting thereof Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A particle processing device, comprising:
   a substrate rotatable with respect to the middle region thereof; and
   at least one fluidic path provided in the substrate to extend from the middle region to a peripheral region and transferring a fluid having a particle from an input portion to an output portion of the fluidic path by using a centrifugal force of the rotation of the substrate,
   wherein a capturing region is formed between the input portion and the output portion of the fluidic path to have a changeable sectional shape for capturing the particle,
   wherein the sectional area of the capturing region is decreased gradually along the extending direction of the fluidic path.

2. The device of claim 1, wherein the capturing region has a sectional dimension smaller than the minimum size of the particle that is deformed under a local pressure due to the physical characteristics of the particle such as deformability or stiffness.

3. The device of claim 1, wherein the sectional shape of the fluidic path is symmetric or asymmetric.

4. The device of claim 1, wherein the fluidic path extends to be straight or spiral from the middle region to the peripheral region of the substrate.

5. The device of claim 1, wherein the rotational velocity, rotational acceleration or rotational direction of the substrate is changed to control the flow velocity of the fluid.

6. The device of claim 1, wherein the fluidic path is a flexible fluidic path.

7. The device of claim 6, wherein the sectional shape of the flexible fluidic path is symmetric or asymmetric.

8. The device of claim 6, wherein the flexible fluidic path extends to be straight or spiral from the middle region to the peripheral region of the substrate.

9. The device of claim 6, further comprising a flexible layer that forms a sidewall of the flexible fluidic path and defines the capturing region.

10. The device of claim 9, wherein the flexible layer comprises
    a fixing portion fixed to a sidewall of the fluidic path; and
    a moving portion extending from the fixing portion and configured to be bent by the rotation of the substrate.

11. The device of claim 9, wherein the rotational velocity, rotational acceleration or rotational direction of the substrate is changed to control the sectional area of the fluidic path and the flow velocity of the fluid.

12. The device of claim 1, wherein a plurality of the fluidic paths is provided in parallel with one another in the substrate.

13. The device of claim 12, further comprising a common input/output portion that is provided in the middle region of the substrate to be connected to the input portions of the fluidic paths.

14. The device of claim 1, further comprising a counter that is arranged in any one of the input portion and the output portion of the fluidic path to detect the number of the particles.

15. The device of claim 1, wherein a collecting fluid flows from the output portion to the input portion of the fluidic path to collect the particle that is captured in the capturing region of the fluidic path.

16. The device of claim 1, wherein a biochemical material layer is formed on an inner surface of the fluidic path or the inner surface of the fluidic path is biochemically or physically changed in order to increase or decrease the adhesive strength with the particle.

* * * * *